United States Patent
Lokai et al.

(10) Patent No.: US 6,839,375 B1
(45) Date of Patent: Jan. 4, 2005

(54) ON-LINE QUALITY CONTROL OF THE KEY OPTICAL COMPONENTS IN LITHOGRAPHY LASERS USING LASER INDUCED FLUORESCENCE

(75) Inventors: Peter Lokai, Goettingen (DE); Farid Seddighi, Goettingen (DE)

(73) Assignee: Lambda Physik AG, Goettingen (DE)

(*) Notice: Subject to any disclaimer, the term of this patent is extended or adjusted under 35 U.S.C. 154(b) by 98 days.

(21) Appl. No.: 10/236,036

(22) Filed: Sep. 4, 2002

Related U.S. Application Data

(60) Provisional application No. 60/317,766, filed on Sep. 6, 2001.

(51) Int. Cl.[7] .......................... H01S 3/08; G01N 21/25; H01J 65/08
(52) U.S. Cl. ........................ 372/92; 356/417; 250/458.1
(58) Field of Search .................. 356/317–318, 356/417; 250/458.1; 372/92–107

(56) References Cited

U.S. PATENT DOCUMENTS

| | | | | |
|---|---|---|---|---|
| 3,975,098 A | * | 8/1976 | West ........................ 356/318 |
| 5,051,162 A | * | 9/1991 | Kambara et al. ............ 204/612 |
| 5,054,878 A | * | 10/1991 | Gergely et al. .............. 385/33 |
| 5,062,942 A | * | 11/1991 | Kambara et al. ............ 204/612 |
| 5,194,913 A | * | 3/1993 | Myrick et al. .............. 356/301 |
| 5,290,419 A | * | 3/1994 | Kambara et al. ............ 204/612 |
| 5,307,148 A | * | 4/1994 | Kambara et al. ............ 356/344 |
| 5,424,841 A | * | 6/1995 | Van Gelder et al. ......... 356/417 |
| 5,485,269 A | * | 1/1996 | Feldman .................... 356/318 |
| 5,516,692 A | * | 5/1996 | Berndt ..................... 435/286.7 |
| 5,830,138 A | * | 11/1998 | Wilson ...................... 600/327 |
| 5,894,352 A | | 4/1999 | Morton ...................... 356/432 |
| 5,926,271 A | * | 7/1999 | Couderc et al. ............ 356/318 |
| 6,002,137 A | * | 12/1999 | Hayashi .................... 250/458.1 |
| 6,058,739 A | | 5/2000 | Morton et al. .............. 65/30.1 |
| 6,075,611 A | * | 6/2000 | Dussan V. et al. .......... 356/432 |
| 6,144,448 A | * | 11/2000 | Mitoma ..................... 356/317 |
| 6,191,425 B1 | * | 2/2001 | Imai ........................ 250/458.1 |
| 6,363,094 B1 | * | 3/2002 | Morton et al. ............... 372/59 |
| 6,389,045 B1 | | 5/2002 | Mann et al. ................. 372/25 |
| 6,542,243 B2 | | 4/2003 | Kramer ...................... 356/450 |
| 6,587,202 B2 | | 7/2003 | Rebhan ..................... 356/432 |
| 6,665,072 B2 | * | 12/2003 | Hoyt ........................ 356/417 |
| 6,704,109 B2 | * | 3/2004 | Wu et al. ................... 356/417 |
| 2002/0021730 A1 | | 2/2002 | Schroeder et al. ........... 372/57 |
| 2002/0139936 A1 | * | 10/2002 | Dumas ...................... 250/458.1 |

OTHER PUBLICATIONS

Leclerc et al., "Transient Absorption and Fluorescence Spectroscopy in Fused Silica Induced by Pulsed KrF Excimer Laser Irradiation," Appl. Phys. Lett. 59(26), Dec. 23, 1991, pp. 3369–3371.

* cited by examiner

*Primary Examiner*—Minsun Oh Harvey
*Assistant Examiner*—Phillip Nguyen
(74) *Attorney, Agent, or Firm*—Stallman & Pollock LLP

(57) ABSTRACT

Some of the key optical components of lithography lasers are very sensitive to intensive UV radiation. Intensive UV radiation can cause color center formation in these components. The color centers are reason for laser energy dropping, worse laser-bandwidth and limited life-time. The on-line monitoring of the color-center formation during operation of the lithography lasers detecting laser induced fluorescence and investigation of the fluorescence spectrum can be helpful for maintenance of lithography lasers. The fluorescence signal is analyzed and delivers information about optics quality.

56 Claims, 2 Drawing Sheets

ON-LINE QUALITY CONTROL OF THE KEY OPTICAL COMPONENTS IN LITHOGRAPHY LASERS USING LASER INDUCED FLUORESCENCE

PRIORITY

This application claims the benefit of priority to U.S. Provisional patent application No. 60/317,766, filed Sep. 6, 2001.

BACKGROUND

In the present time is the quality of optical components in lithography systems not on-line tested. The common indicator used for replacement of optics is the laser counter. With the present invention the life-time of these expensive parts can be monitored and analyzed the induced fluorescence in these components during laser operation and the parts will only be exchanged when necessary. All of the following references, as well as the Background, Title and Summary of the Invention, are hereby incorporated by reference into the detailed description of the preferred embodiments as disclosing alternative features and elements not particularly set forth in the detailed description:
1. M. Mizuguuchi et al.: Time-resolved photo luminescence for diagnosis of resistance to ArF excimer laser damage to CaF2 single crystals, J. Opt. Soc. Am. B 16, 1153–1159, 1999
2. L. L. Clarke, M. S. Mendicino: Investigating Excimer Laser Induced Fluorescence in CaF2, 1999
3. Triebel, W. et. al.: Fused Silica Evaluated for Excimer Laser Applications, Euro Photonics, Dec./Jan. 30–31, 2001
4. U.S. Pat. No. 5,894,352
5. U.S. patent application Ser. No. 09/726,871, which is assigned to the same assignee as the present application.

SUMMARY OF THE INVENTION

Some key optical components in lithography lasers (e.g. prisms, etalons, resonator windows, outcoupler etc.) are very sensitive to intensive UV radiation. Color center formation is in progress after LTV illumination of these components. The color centers are reason for laser energy dropping, worse laser-bandwidth and limited life-time.

On-line monitoring of the color-center formation during operation of the lithography lasers detecting laser induced fluorescence and investigation of the fluorescence spectrum can be helpful for maintenance of lithography lasers. Analysis of the detected induced fluorescence (peak wavelength and intensity) gives valuable information about optics quality and reference.

At the present time the laser induced fluorescence is only used in the preselection of suitable substrate materials e.g. fused silica or CaF2 delivered from suppliers.

On-line investigation of the optical components fluorescence in the lithography lasers during their operation is until now not used. Our invention improve the maintenance of these components —indicating quality of these parts during laser operation and giving reference for their replacement.

In view of the above, a fluorescence detection apparatus for monitoring fluorescence of one or more optical components of a laser system, such as including an excimer, molecular fluorine or solid state laser, is provided. The fluorescence detection apparatus includes one or more light wave guides for transmitting the fluorescence of the one or more optical components, a fluorescence detection system for detecting the transmitted fluorescence, and an evaluation apparatus for analyzing the detected fluorescence. The system may further including one or more imaging systems collecting fluorescence to be transmitted.

The one or more light wave guides may transmit the fluorescence directly to the fluorescence detection system. The fluorescence detection system may include an optical filter such as a sharp cut filter or an interference filter. The fluorescence detection system may include a radiation sensitive detector such as a photodiode or photomultiplier. The fluorescence detection system may include a peak detector such as a box-car detector for detecting the formation of fluorescence at visible wavelengths.

The evaluation system may include a data processing unit. The evaluation system may analyze the detected fluorescence on-line during laser operation.

The one or more optical components may include one or more of a laser resonator window, a prism, an etalon or other interferometric device (see, e.g., U.S. Pat. No. 6,421,365, hereby incorporated by reference), a beam splitter, and/or a polarizer.

The laser system may include an ArF, KrF, $F_2$, XeCl or XeF laser, among others including a solid state laser system that may include a harmonic crystal.

DETAILED DESCRIPTION OF THE PREFERRED EMBODIMENTS

Some key optical component in lithography lasers (e.g. Prisms, Etalons, resonator windows, outcoupler etc.) are very sensitive to intensive UV radiation. Color center formation is in progress after UV illumination of these components. The color centers are reason for laser energy dropping, worse laser-bandwidth and limited live-time. To reduce the cost of ownership, the life time of optical components is an important parameter, mainly for high repetition lithography lasers used in steppers or scanners.

On-line monitoring of the color-center formation during operation of the lithography lasers detecting the induced fluorescence and investigation of the fluorescence spectrum can be helpful for maintenance of lithography lasers. Analysis of the detected induced fluorescence (peak wavelength, numbers of peak and their intensity) gives valuable information about optics quality, and reference for an eventually replacement (green and/or red fluorescence bands formation).

Figure 1:
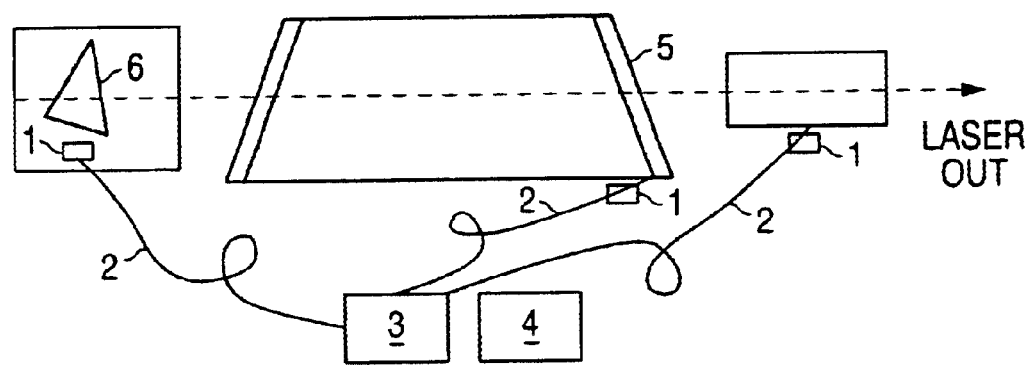
FIG. 1 schematically illustrates a laser system including a fluorescence detection apparatus in accordance with a preferred embodiment.

In FIG. 1 the fluorescence detection apparatus which is mounted inside the excimer laser or solid state laser is shown. The fluorescence light which is caused by the laser beam itself is collected from the exposed fluorescent optical parts into preferably a flexible light wave guide (2). Alternatively, another light collection means (2) for collecting the fluorescence light may be used as understood by those skilled in the art, e.g., a non-flexible light wave guide such as may be made of metal or hard plastic, a series of lenses and/or a system wherein the detection equipment is brought close to the optics such that neither a flexible nor non-flexible light guide is used. What is meant by "light wave guide" herein, including in the claims, then, is any optical unit or positioning or configuring of the fluorescence detection apparatus that facilitates and/or allows the fluorescence light to reach the detection unit (3) for monitoring. Experiments have shown that the imaging system (1) is only necessary when the fluorescence is weak. Usually the fluorescence is so strong that the light wave guide (2) can easily brought in the vicinity of the examined optical parts. The fluorescence light is transmitted through the light wave guide to a fluorescence detection unit (3) and the signal is evaluated by an evaluation apparatus (4). The optical imaging system (1) consists of one or more plan convex lenses. The fluorescence detection unit (3) consists of an optical filter, e.g. a sharp cut filter or an interference filter. Further a radiation sensitive detector like a photodiode or photomultiplier is used and a peak detector (box-car) is installed to detect the formation of the fluorescence at longer wavelengths (e.g. green and/or yellow and/or red) where the formation of color centers strongly affect the quality of the optical parts. The fluorescence detection system further consists of a monochromator, e.g. a grating or prism, and a photodiode array to detect the whole UV-, VIS-, NIR-range of the fluorescence spectrum. With the above described fluorescence detection apparatus laser resonator windows (5), tuning elements like prisms (6) or etalons (6), beam splitters, polarizers and all other optical parts which are made of fused silica or UV transmissive crystal material (e.g. $CaF_2$, $MgF_2$ etc.) which are in the laser and directly illuminated during laser operation can be examined and analyzed.

This fluorescence detection apparatus can be used for ArF, KrF, $F_2$ lasers which are presently mainly used in lithography or in industrial high power XeF, XeCl, KrCl, KrF or ArF lasers. The above described fluorescence detection apparatus can also be used to detect the fluorescence of the harmonics crystals (like SHG, THG, FHG) in solid state lasers. This on-line control technique described above can reduce laser downtimes because the service engineer or the customer can control the state of the optical parts at any time and in the case the fluorescence starts to increase the parts can be changed during the next planned service downtime. So the time and costs to search for worse laser performance can be minimized.

Overall Laser System

Figure 2:
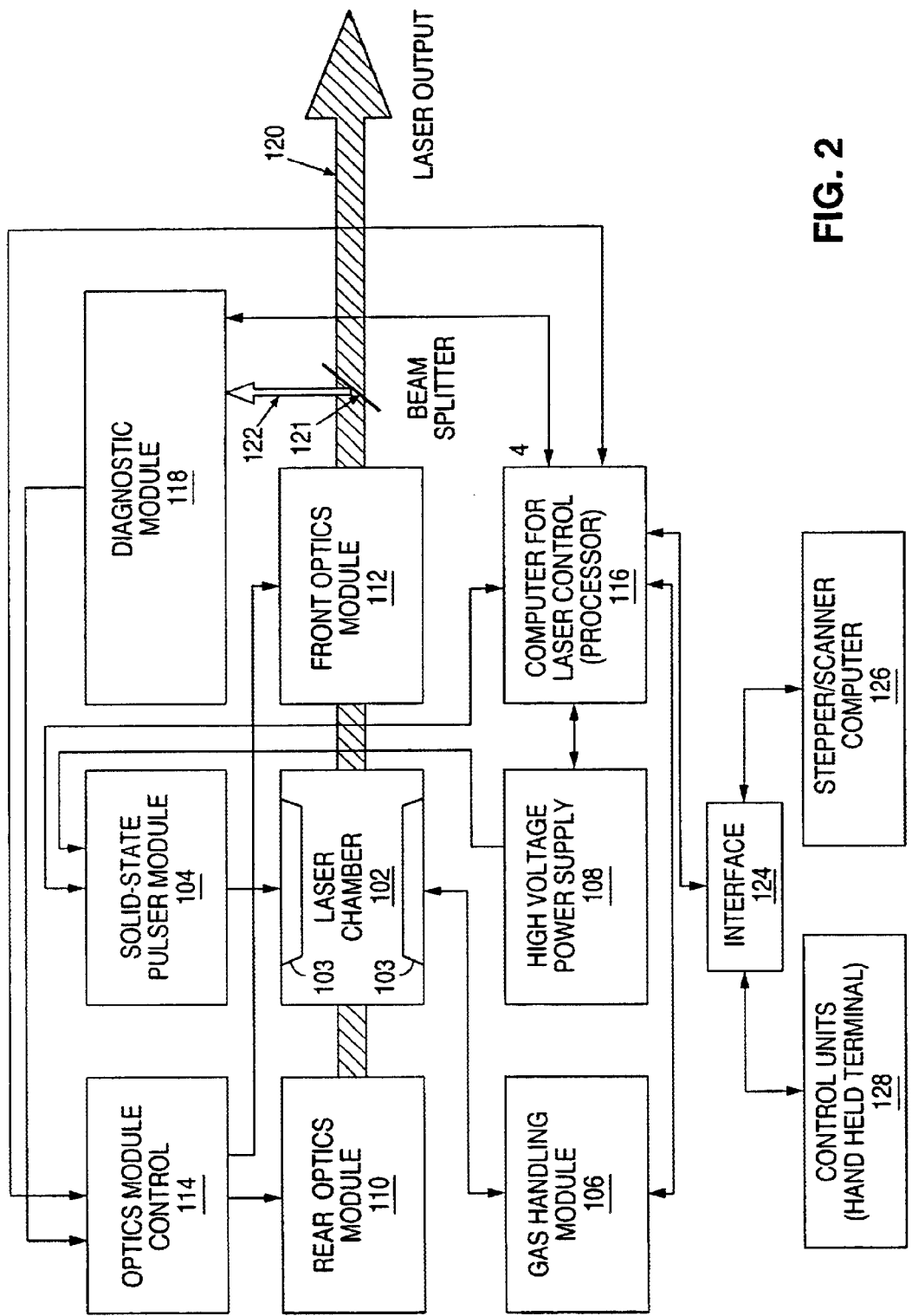
FIG. 2 generally illustrates an overall excimer or molecular laser system in accordance with a preferred embodiment.

FIG. 2 schematically illustrates an overall excimer or molecular fluorine laser system according to a preferred embodiment which preferably includes the advantageous features described above with reference to FIG. 1. Referring to FIG. 2, a preferred excimer or molecular fluorine laser system is a DUV or VUV laser system, such as a KrF, ArF or molecular fluorine (F2) laser system, for use with a deep ultraviolet (DUV) or vacuum ultraviolet (VUV) lithography system. Alternative configurations for laser systems for use in such other industrial applications as TFT annealing, photoablation and/or micromachining, e.g., include configurations understood by those skilled in the art as being similar to and/or modified from the system shown in FIG. 2 to meet the requirements of that application. For this purpose, alternative DUV or VUV laser system and component configurations are described at U.S. patent application Ser. Nos. 09/317,695, 09/244,554, 09/452,353, 09/512,417, 09/599, 130, 09/694,246, 09/712,877, 09/574,921, 09/738,849, 09/718,809, 09/629,256, 09/712,367, 09/771,366, 09/715, 803, 09/738,849, 09/791,431, 60/204,095, 09/741,465, 09/574,921, 09/734,459, 09/741,465, 09/686,483, 09/584, 420, 09/843,604, 09/780,120, 09/792,622, 09/791,431, 09/811,354, 09/838,715, 09/715,803, 09/717,757, 09/771, 013, 09/791,430, 09/712,367 and 09/780,124, and U.S. Pat. Nos. 6,285,701, 6,005,880, 6,061,382, 6,020,723, 6,219, 368, 6,212,214, 6,154,470, 6,157,662, 6,243,405, 6,243,406, 6,198,761, 5,946,337, 6,014,206, 6,157,662, 6,154,470, 6,160,831, 6,160,832, 5,559,816, 4,611,270, 5,761,236, 6,212,214, 6,243,405, 6,154,470, and 6,157,662, each of which is assigned to the same assignee as the present application and is hereby incorporated by reference.

Discharge Tube

The system shown in FIG. 2 generally includes a laser chamber 102 (or laser tube including a heat exchanger and fan for circulating a gas mixture within the chamber 102 or tube) having a pair of main discharge electrodes 103 connected with a solid-state pulser module 104, and a gas handling module 106. The gas handling module 106 has a valve connection to the laser chamber 102 so that halogen, any active rare gases and a buffer gas or buffer gases, and optionally a gas additive, may be injected or filled into the laser chamber, preferably in premixed forms (see U.S. patent application Ser. Nos. 09/513,025, 09/780,120, 09/734,459 and 09/447,882, which are assigned to the same assignee as the present application, and U.S. Pat. Nos. 4,977,573, 4,393, 505 and 6,157,662, which are each hereby incorporated by reference. The solid state pulser module 104 is powered by a high voltage power supply 108. A thyratron pulser module may alternatively be used. The laser chamber 102 is surrounded by optics module 110 and optics module 112, forming a resonator. The optics modules 110 and 112 may be controlled by an optics control module 114, or may be alternatively directly controlled by a computer or processor 116, particular when line-narrowing optics are included in one or both of the optics modules 1l 110, 11 1-2, such as is preferred when KrF, ArF or F2 lasers are used for optical lithography.

Processor Control

The processor 116 for laser control receives various inputs and controls various operating parameters of the system. A diagnostic module 118 receives and measures one or more parameters, such as pulse energy, average energy and/or power, and preferably wavelength, of a split off portion of the main beam 120 via optics for deflecting a small portion 122 of the beam toward the module 118, such as preferably a beam splitter module 121. The beam 120 is preferably the laser output to an imaging system (not shown) and ultimately to a workpiece (also not shown) such as particularly for lithographic applications, and may be output directly to an application process. The laser control computer 116 may communicate through an interface 124 with a stepper/scanner computer, other control units 126, 128 and/or other external systems.

The processor or control computer 116 receives and processes values of some of the pulse shape, energy, ASE, energy stability, energy overshoot for burst mode operation, wavelength, spectral purity and/or bandwidth, among other input or output parameters of the laser system and output beam. The processor may receive signals corresponding to the wavefront compensation such as values of the bandwidth, and may control the wavefront compensation performed by the wavefront compensation optic 3, 13, 23 (see above) in a feedback loop by sending signals to adjust the pressure(s) and/or curvature(s) of surfaces associated with the wavefront compensation optic 3, 13, 23. The processor 116 also controls the line narrowing module to tune the wavelength and/or bandwidth or spectral purity, and controls the power supply and pulser module 104 and 108 to control preferably the moving average pulse power or energy, such that the energy dose at points on the workpiece is stabilized around a desired value. In addition, the computer 116 controls the gas handling module 106 which includes gas supply valves connected to various gas sources. Further functions of the processor 116 such as to provide overshoot control, energy stability control and/or to monitor input energy to the discharge, are described in more detail at U.S. patent application Ser. No. 09/588,561, which is assigned to the same assignee and is hereby incorporated by reference.

As shown in FIG. 2, the processor 116 preferably communicates with the solid-state or thyratron pulser module 104 and HV power supply 108, separately or in combination, the gas handling module 106, the optics modules 110 and/or 112, the diagnostic module 118, and an interface 124. The laser resonator which surrounds the laser chamber 102 containing the laser gas mixture includes optics module 110 including line-narrowing optics for a line narrowed excimer or molecular fluorine laser, which may be replaced by a high reflectivity mirror or the like in a laser system wherein either line-narrowing is not desired, or if line narrowing is performed at the front optics module 112, or a spectral filter external to the resonator is used for narrowing the linewidth of the output beam.

Solid State Pulser Module

The laser chamber 102 contains a laser gas mixture and includes one or more preionization units (not shown) in addition to the pair of main discharge electrodes 103. Preferred main electrodes 103 are described at U.S. patent application Ser. No. 09/453,670 for photolithographic applications, which is assigned to the same assignee as the present application and is hereby incorporated by reference, and may be alternatively configured, e.g., when a narrow discharge width is not preferred. Other electrode configurations are set forth at U.S. Pat. Nos. 5,729,565 and 4,860,300, each of which is assigned to the same assignee, and alternative embodiments are set forth at U.S. Pat. Nos. 4,691,322, 5,535,233 and 5,557,629, all of which are hereby incorporated by reference. Preferred preionization units may be sliding surface or corona-type and are described U.S. patent application Ser. Nos. 09/922,241 and 09/532,276 (sliding surface) and Ser. Nos. 09/692,265 and 09/247,887 (corona discharge), each of which is assigned to the same assignee as the present application, and additional alternative embodiments are set forth at U.S. Pat. Nos. 5,337,330, 5,818,865, 5,875,207 and 5,991,324, and German Gebrauchsmuster DE 295 21 572 U1, all of the above patents and patent applications being hereby incorporated by reference.

The solid-state or thyratron pulser module 104 and high voltage power supply 108 supply electrical energy in compressed electrical pulses to the preionization and main electrodes 103 within the laser chamber 102 to energize the gas mixture. Components of the preferred pulser module and high voltage power supply are described above, and further details may be described at U.S. patent application Ser. Nos. 09/640,595, 09/838,715, 60/204,095, 09/432,348 and 09/390,146, and U.S. Pat. Nos. 6,005,880, 6,226,307 and 6,020,723, each of which is assigned to the same assignee as the present application and which is hereby incorporated by reference into the present application. Other alternative pulser modules are described at U.S. Pat. Nos. 5,982,800, 5,982,795, 5,940,421, 5,914,974, 5,949,806, 5,936,988, 6,028,872, 6,151,346 and 5,729,562, each of which is hereby incorporated by reference.

Resonator, General

The laser resonator which surrounds the laser chamber 102 containing the laser gas mixture includes optics module 110 preferably including line-narrowing optics for a line narrowed excimer or molecular fluorine laser such as for photolithography, which may be replaced by a high reflectivity mirror or the like in a laser system wherein either line-narrowing is not desired (for TFT annealling, e.g.), or if line narrowing is performed at the front optics module 112, or a spectral filter external to the resonator is used, or if the line-narrowing optics are disposed in front of the HR mirror, for narrowing the bandwidth of the output beam. For an F2-laser, optics for selecting one of multiple lines around 157 nm may be used, e.g., one or more dispersive prisms, birefringent plates or blocks and/or an interferometric device such as an etalon or a device having a pair of opposed, non-parallel plates such as described in the Ser. No. 09/715,803 and 60/280,398 applications, wherein the same optic or optics or an additional line narrowing optic or optics for narrowing the selected line may be used. Also, particularly for the F2-laser, and also possibly for other excimer lasers, the total gas mixture pressure may be lower than conventional systems, e.g., lower than 3 bar, for producing the selected line at a narrow bandwidth such as 0.5 pm or less without using additional line-narrowing optics (see U.S. patent application No. 60/212,301, which is assigned to the same assignee as the present application and is hereby incorporated by reference).

The laser chamber 102 is sealed by windows transparent to the wavelengths of the emitted laser radiation 120. The windows may be Brewster windows or may be aligned at another angle, e.g., 5', to the optical path of the resonating beam. One of the windows may also serve to output couple the beam or as a highly reflective resonator reflector on the opposite side of the chamber 102 as the beam is outcoupled.

Diagnostic Module

After a portion of the output beam 120 passes the outcoupler of the optics module 112, that output portion preferably impinges upon a beam splitter module 121 which includes optics for deflecting a portion 122 of the beam to the diagnostic module 118, or otherwise allowing a small portion 122 of the outcoupled beam to reach the diagnostic module 118, while a main beam portion 120 is allowed to continue as the output beam 120 of the laser system (see U.S. patent application Ser. Nos. 09/771,013, 09/598,552, and 09/712,877 which are assigned to the same assignee as the present invention, and U.S. Pat. No. 4,611,270, each of which is hereby incorporated by reference. Preferred optics include a beamsplitter or otherwise partially reflecting surface optic. The optics may also include a mirror or beam splitter as a second reflecting optic. More than one beam splitter and/or HR mirror(s), and/or dichroic mirror(s) may be used to direct portions of the beam to components of the diagnostic module 118. A holographic beam sampler, transmission grating, partially transmissive reflection diffraction grating, grism, prism or other refractive, dispersive and/or transmissive optic or optics may also be used to separate a small beam portion from the main beam 120 for detection at the diagnostic module 118, while allowing most of the main beam 120 to reach an application process directly or via an imaging system or otherwise. These optics or additional optics may be used to filter out visible radiation such as the red emission from atomic fluorine in the gas mixture from the split off beam prior to detection.

The output beam 120 may be transmitted at the beam splitter module while a reflected beam portion is directed at the diagnostic module 118, or the main beam 120 may be reflected, while a small portion is transmitted to the diagnostic module 118. The portion of the outcoupled beam which continues past the beam splitter module 121 is the output beam 120 of the laser, which propagates toward an industrial or experimental application such as an imaging system and workpiece for photolithographic applications.

The diagnostic module 118 preferably includes at least one energy detector. This detector measures the total energy of the beam portion that corresponds directly to the energy of the output beam 120 (see U.S. Pat. Nos. 4,611,270 and 6,212,214 which are hereby incorporated by reference). An optical configuration such as an optical attenuator, e.g., a plate or a coating, or other optics may be formed on or near the detector or beam splitter module 121 to control the intensity, spectral distribution and/or other parameters of the radiation impinging upon the detector (see U.S. patent application Ser. Nos. 09/172,805, 09/741,465, 09/712,877, 09/771,013 and 09/771,366, each of which is assigned to the same assignee as the present application and is hereby incorporated by reference).

One other component of the diagnostic module 118 is preferably a wavelength and/or bandwidth detection component such as a monitor etalon or grating spectrometer, and a hollow cathode lamp or reference light source for providing absolute wavelength calibration of the monitor etalon or grating spectrometer (see U.S. patent application Ser. Nos. 09/416,344, 09/686,483, and 09/791,431, each of which is assigned to the same assignee as the present application, and U.S. Pat. Nos. 4,905,243, 5,978,391, 5,450,207, 4,926,428, 5,748,346, 5,025,445, 6,160,832, 6,160,831, 6,269,110, 6,272,158 and 5,978,394, all of the above wavelength and/or bandwidth detection and monitoring components being hereby incorporated by reference). The bandwidth and/or wavelength or other spectral, energy or other beam parameter may be monitored and controlled in a feedback loop including the processor 116 and optics control modules 110, 112, gas handling module 106, power supply and pulser modules 103, 104, or other laser system component modules. For example, the total pressure of the gas mixture in the laser tube 102 may be controlled to a particular value for producing an output beam at a particular bandwidth and/or energy.

Other components of the diagnostic module may include a pulse shape detector or ASE detector, such as are described at U.S. Pat. Nos. 6,243,405 and 6,243,406 and U.S. patent application Ser. No. 09/842,281, which is assigned to the same assignee as the present application, each of which are hereby incorporated by reference, such as for gas control and/or output beam energy stabilization, or to monitor the amount of amplified spontaneous emission (ASE) within the beam to ensure that the ASE remains below a predetermined level. There may be a beam alignment monitor, e.g., such as is described at U.S. Pat. No. 6,014,206, or beam profile monitor, e.g., U.S. patent application Ser. No. 09/780,124, which is assigned to the same assignee, wherein each of these patent documents is hereby incorporated by reference.

Beam Path Enclosure

Particularly for the molecular fluorine laser system, and also for the ArF and KrF laser systems, an enclosure (not shown) preferably seals the beam path of the beam 120 such as to keep the beam path free of photoabsorbing or other contaminant species that can tend to attenuate and/or otherwise disturb the beam such as by providing a varying refractive-index along the optical path of the beam. Smaller enclosures preferably seal the beam path between the chamber 102 and the optics modules 110 and 112 and between the beam splitter 122 and the diagnostic module 118 (see the Ser. Nos. 09/317,695, 09/594,892 and 09/598,552 applications, incorporated by reference above). The optics modules 110 and 112 are maintained in an atmosphere that is sufficiently evacuated or have an inert gas purged atmosphere. Preferred enclosures are described in detail in U.S. patent application Ser. Nos. 09/598,552, 09/594,892, 09/727,600, 09/317,695 and 09/131,580, which are assigned to the same assignee and are hereby incorporated by reference, and U.S. Pat. Nos. 6,219,368, 5,559,584, 5,221, 823, 5,763,855, 5,811,753 and 4,616,908, all of which are hereby incorporated by reference.

Gas Mixture

The laser gas mixture is initially filled into the laser chamber 102 in a process referred to herein as a "new fills". In such procedure, the laser tube evacuated of laser gases and contaminants, and re-filled with an ideal gas composition of fresh gas. The gas composition for a very stable excimer or molecular fluorine laser in accord with the preferred embodiment uses helium or neon or a mixture of helium and neon as buffer gas(es), depending on the particular laser being used. Preferred gas compositions are described at U.S. Pat. Nos. 4,393,405, 6,157,162, 6,243,406 and 4,977,573 and U.S. patent application Ser. Nos. 09/513, 025, 09/447,882, 09/789,120 and 09/588,561, each of which is assigned to the same assignee and is hereby incorporated by reference into the present application. The concentration of the fluorine in the gas mixture may range from 0.003% to 1.00%, and is preferably around 0.1%. An additional gas additive, such as a rare gas or otherwise, may be added for increased energy stability, overshoot control and/or as an attenuator as described in the Ser. No. 09/513,025 application incorporated by reference above. Specifically, for the F2 laser, an addition of xenon, krypton and/or argon may be used. The concentration of xenon or argon in the mixture may range from 0.0001% to 0.1%. For an ArF-laser, an addition of xenon or krypton may be used also having a concentration between 0.0001% to 0.1%. For the KrF laser, an addition of xenon or argon may be used also having a concentration between 0.0001% to 0.1%. Gas replenishment actions are described below for gas mixture compositions of systems such as ArF, KrF, and XeCl excimer lasers and molecular fluorine lasers, wherein the ideas set forth herein may be advantageously incorporated into any of these systems, and other gas discharge laser systems.

Gas Replenishment

Halogen gas injections, including micro-halogen injections of, e.g., 1–3 milliliters of halogen gas, mixed with, e.g., 20–60 milliliters of buffer gas or a mixture of the halogen gas, the buffer gas and a active rare gas for rare gas-halide excimer lasers, per injection for a total gas volume in the laser tube 102 of, e.g., 100 liters, total pressure adjustments and gas replacement procedures may be performed using the gas handling module 106 preferably including a vacuum pump, a valve network and one or more gas compartments. The gas handling module 106 receives gas via gas lines connected to gas containers, tanks, canisters and/or bottles. Some preferred and alternative gas handling and/or replenishment procedures, other than as specifically described herein (see below), are described at U.S. Pat. Nos. 4,977, 573, 6,212,214, 6,243,406 and 5,396,514 and U.S. patent application Ser. Nos. 09/447,882, 09/734,459, 09/513,025 and 09/588,561, each of which is assigned to the same assignee as the present application, and U.S. Pat. Nos. 5,978,406, 6,014,398 and 6,028,880, all of which are hereby incorporated by reference. A xenon gas or other gas additive supply may be included either internal or external to the laser system according to the '025 application, mentioned above.

Total pressure adjustments in the form of releases of gases or reduction of the total pressure within the laser tube 102 may also be performed. Total pressure adjustments may be followed by gas composition adjustments if it is determined that, e.g., other than the desired partial pressure of halogen gas is within the laser tube 102 after the total pressure adjustment. Total pressure adjustments may also be performed after gas replenishment actions, and may be performed in combination with smaller adjustments of the driving voltage to the discharge than would be made if no pressure adjustments were performed in combination.

Gas replacement procedures may be performed and may be referred to as partial, mini- or macro-gas replacement operations, or partial new fill operations, depending on the amount of gas replaced, e.g., anywhere from a few milliliters up to 50 liters or more, but less than a new fill, such as are set forth in the Ser. No. 09/734,459 application, incorporated by reference above. As an example, the gas handling unit 106 connected to the laser tube 102 either directly or through an additional valve assembly, such as may include a small compartment for regulating the amount of gas injected (see the '459 application), may include a gas line for injecting a premix A including 1% F2:99% Ne or other buffer gas such as He, and another gas line for injecting a premix B including 1% rare gas:99% buffer gas, for a rare gas-halide excimer laser, wherein for a F2 laser premix B is not used. Another line may be used for injecting a gas additive or gas additive premix, or a gas additive may be added to premix A, premix B or a buffer gas. Another line may be used for total pressure additions or reductions, i.e., for flowing buffer gas into the laser tube or allowing some of the gas mixture in the tube to be released, possibly accompanying halogen injections for maintaining the halogen concentration. Thus, by injecting premix A (and premix B for rare gas-halide excimer lasers) into the tube 102 via the valve assembly, the fluorine concentration in the laser tube 102 may be replenished. Then, a certain amount of gas may be released corresponding to the amount that was injected to maintain the total pressure at a selected level. Additional gas lines and/or valves may be used for injecting additional gas mixtures. New fills, partial and mini gas replacements and gas injection procedures, e.g., enhanced and ordinary micro-halogen injections, such as between 1 milliliter or less and 3–10 milliliters, or more depending on the degree of stability desired, and any and all other gas replenishment actions are initiated and controlled by the processor 116 which controls valve assemblies of the gas handling unit 106 and the laser tube 102 based on various input information in a feedback loop. These gas replenishment procedures may be used in combination with gas circulation loops and/or window replacement procedures to achieve a laser system having an increased servicing interval for both the gas mixture and the laser tube windows.

Line Narrowing

A general description of the line-narrowing features of embodiments of the laser system particularly for use with photolithographic applications is provided here, followed by a listing of patent and patent applications being incorporated by reference as describing variations and features that may be used within the scope of the preferred embodiments herein for providing an output beam with a high spectral purity or bandwidth (e.g., below 1 pm and preferably 0.6 pm or less). These exemplary embodiments may be used along with the wavefront compensating optic 3, 13, 13 described above. For the F2 laser, the optics may be used for selecting the primary line $\lambda 1$, only of multiple lines around 157 nm, or may be used to provide additional line narrowing as well as performing line-selection, or the resonator may include optics for line-selection and additional optics for line-narrowing of the selected line, and line-narrowing may be provided by controlling (i.e., reducing) the total pressure (see U.S. patent application No. 60/212,301, which is assigned to the same assignee and is hereby incorporated by reference). Line-narrowing of the broadband emission of the ArF and/or KrF lasers may be as set forth below.

Exemplary line-narrowing optics contained in the optics module 110 include a beam expander, an optional interferometric device such as an etalon or a device having a pair of opposed non-planar reflection plates such as may be described in the Ser. No. 09/715,803 or 60/280,398 applications, which are assigned to the same assignee as the present application and are hereby incorporated by reference, and a diffraction grating, and alternatively one or more dispersion prisms may be used, wherein the grating would produce a relatively higher degree of dispersion than the prisms although generally exhibiting somewhat lower efficiency than the dispersion prism or prisms, for a narrow band laser such as is used with a refractive or catadioptric optical lithography imaging system. As mentioned above, the front optics module may include line-narrowing optics such as may be described in any of the Ser. Nos. 09/715,803, 09/738,849, and 09/718,809 applications, each being assigned to the same assignee and hereby incorporated by reference.

Instead of having a retro-reflective grating in the rear optics module 110, the grating may be replaced with a highly reflective mirror, and a lower degree of dispersion may be produced by a dispersive prism, or a beam expander and an interferometric device such as an etalon or device having non-planar opposed plates may be used for line-selection and narrowing, or alternatively no line narrowing or line-selection may be performed in the rear optics module 110. In the case of using an all-reflective imaging system, the laser may be configured for semi-narrow band operation such as having an output beam linewidth in excess of 0.5 pm, depending on the characteristic broadband bandwidth of the laser, such that additional line-narrowing of the selected line would not be used, either provided by optics or by reducing the total pressure in the laser tube.

The beam expander of the above exemplary line-narrowing optics of the optics module 110 preferably includes one or more prisms. The beam expander may include other beam expanding optics such as a lens assembly or a converging/diverging lens pair. The grating or a highly reflective mirror is preferably rotatable so that the wavelengths reflected into the acceptance angle of the resonator can be selected or tuned. Alternatively, the grating, or other optic or optics, or the entire line-narrowing module may be pressure tuned, such as is set forth in the Ser. No. 09/771,366 application and the U.S. Pat. No. 6,154,470, each of which is assigned to the same assignee and is hereby incorporated by reference. The grating may be used both for dispersing the beam for achieving narrow bandwidths and also preferably for retroreflecting the beam back toward the laser tube. Alternatively, a highly reflective mirror is positioned after the grating which receives a reflection from the grating and reflects the beam back toward the grating in a Littman configuration, or the grating may be a transmission grating. One or more dispersive prisms may also be used, and more than one etalon or other interferometric device may be used.

Depending on the type and extent of line-narrowing and/or selection and tuning that is desired, and the particular laser that the line-narrowing optics are to be installed into, there are many alternative optical configurations that may be used. For this purpose, those shown in U.S. Pat. Nos. 4,399,540, 4,905,243, 5,226,050, 5,559,816, 5,659,419, 5,663,973, 5,761,236, 6,081,542, 6,061,382, 6,154,470, 5,946,337, 5,095,492, 5,684,822, 5,835,520, 5,852,627, 5,856,991, 5,898,725, 5,901,163, 5,917,849, 5,970,082, 51,404,366, 4,975,919, 5,142,543, 5,596,596, 5,802,094, 4,856,018, 5,970,082, 5,978,409, 5,999,318, 5,150,370 and 4,829,536, and German patent DE 298 22 090.3, and any of the patent applications mentioned above and below herein, may be consulted to obtain a line-narrowing configuration that may be used with a preferred laser system herein, and each of these patent references is each hereby incorporated by reference into the present application.

Additional Laser System Features

Optics module 112 preferably includes means for outcoupling the beam 120, such as a partially reflective resonator reflector. The beam 120 may be otherwise outcoupled such as by an intra-resonator beam splitter or partially reflecting surface of another optical element, and the optics module 112 would in this case include a highly reflective mirror. The optics control module 114 preferably controls the optics modules 110 and 112 such as by receiving and interpreting signals from the processor 116, and initiating realignment, gas pressure adjustments in the modules 110, 112, or reconfiguration procedures (see the '353, '695, '277, '554, and '527 applications mentioned above).

The halogen concentration in the gas mixture is maintained constant during laser operation by gas replenishment actions by replenishing the amount of halogen in the laser tube for the preferred excimer or molecular fluorine laser herein, such that these gases are maintained in a same predetermined ratio as are in the laser tube 102 following a new fill procedure. In addition, gas injection actions such as $\mu$Hls as understood from the '882 application, mentioned above, may be advantageously modified into micro gas replacement procedures, such that the increase in energy of the output laser beam may be compensated by reducing the total pressure. In addition, the laser system is preferably configured for controlling the input driving voltage so that the energy of the output beam is at the predetermined desired energy. The driving voltage is preferably maintained within a small range around $HV_{opt}$, while the gas procedure operates to replenish the gases and maintain the average pulse energy or energy dose, such as by controlling an output rate of change of the gas mixture or a rate of gas flow through the laser tube 102. Advantageously, the gas procedures set forth herein permit the laser system to operate within a very small range around $HV_{opt}$, while still achieving average pulse energy control and gas replenishment, and increasing the gas mixture lifetime or time between new fills (see U.S. patent application Ser. No. 09/780,120, which is assigned to the same assignee as the present application and is hereby incorporated by reference).

In all of the above and below embodiments, the material used for any dispersive prisms, the prisms of any beam expanders, etalons or other interferometric devices, laser windows and the outcoupler is preferably one that is highly transparent at excimer or molecular fluorine laser wavelengths such as 248 nm for the KrF laser, 193 nm for the ArF laser and 157 nm for the F2 laser. The materials are also capable of withstanding long-term exposure to ultraviolet light with minimal degradation effects. Examples of such materials are CaF2, MgF2, BaF2, LiF and SrF2, and in some cases fluorine-doped quartz may be used, and for the KrF laser, fused silica may be used. Also, in all of the embodiments, many optical surfaces, particularly those of the prisms, may or may not have an anti-reflective coating on one or more optical surfaces, in order to minimize reflection losses and prolong their lifetime.

Also, the gas composition for the excimer or molecular fluorine laser in the above configurations uses either helium, neon, or a mixture of helium and neon as a buffer gas. For rare gas-halide excimer lasers, the rare gas is preferably maintained at a concentration of around 1.0% in the gas mixture. The concentration of fluorine in the gas mixture preferably ranges from 0.003% to around 1.0%, and is preferably around 0.1%. However, if the total pressure is reduced for narrowing the bandwidth, then the fluorine concentration may be higher than 0.1%, such as may be maintained between 1 and 7 mbar, and more preferably around 3–5 mbar, notwithstanding the total pressure in the tube or the percentage concentration of the halogen in the gas mixture. The addition of a trace amount of xenon, and/or argon, and/or oxygen, and/or krypton and/or other gases (see the '025 application) may be used for increasing the energy stability, burst control, and/or output energy of the laser beam. The concentration of xenon, argon, oxygen, or krypton in the mixture as a gas additive may range from 0.0001% to 0.1%, and would be preferably significantly below 0.1%. Some alternative gas configurations including trace gas additives are set forth at U.S. patent application Ser. No. 09/513,025 and U.S. Pat. No. 6,157,662, each of which is assigned to the same assignee and is hereby incorporated by reference.

A line-narrowed oscillator, e.g., a set forth above, may be followed by a power amplifier for increasing the power of the beam output by the oscillator. Preferred features of the oscillator-amplifier set-up are set forth at U.S. patent application Ser. No. 09/599,130 and 60/228,184, which are assigned to the same assignee and are hereby incorporated by reference. The amplifier may be the same or a separate discharge chamber 102. An optical or electrical delay may be used to time the electrical discharge at the amplifier with the reaching of the optical pulse from the oscillator at the amplifier. With particular respect to the 172 laser, a molecular fluorine laser oscillator may have an advantageous output coupler having a transmission interference maximum at X, and a minimum at X2. A 157 nm beam is output from the output coupler and is incident at the amplifier of this embodiment to increase the power of the beam. Thus, a very narrow bandwidth beam is achieved with high suppression of the secondary line X2 and high power (at least several Watts to more than 10 Watts).

While exemplary drawings and specific embodiments of the present invention have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention.

What is claimed is:

1. A fluorescence detection apparatus for monitoring fluorescence of one or more optical components of a laser system, comprising:

(a) at least one optical imaging system positioned to collect fluorescence of at least one of the one or more optical components of the laser system, during the operation of the laser system, wherein the one or more optical components includes at least one selected from the group consisting of one or more laser resonator windows, one or more prisms, one or more etalons, one or more beam splitters, and one or more polarizers;

(b) one or more light wave guides for transmitting the fluorescence of the one or more optical components;

(c) a fluorescence detection system for detecting the transmitted fluorescence; and (d) an evaluation apparatus for analyzing the detected fluorescence.

2. The fluorescence detection apparatus of claim 1, wherein the at least one optical imaging system comprises one or more plan convex lenses to collect the fluorescence of the at least one optical component.

3. The fluorescence detection apparatus of claim 1, wherein the one or more light wave guide transmits the fluorescence directly to the fluorescence detection system.

4. The fluorescence detection apparatus of claim 1, wherein the fluorescence detection system comprises an optical filter.

5. The fluorescence detection apparatus of claim 4, wherein the optical filter includes at least one optical filter selected from the group of optical filters consisting of a sharp cut filter and interference filter.

6. The fluorescence detection apparatus of claim 4, wherein the fluorescence detection system further comprises a radiation sensitive detector.

7. The fluorescene detection apparatus of claim 6, wherein the radiation sensitive detector includes a detector selected from the group consisting of a photodiode and a photomultiplier.

8. The fluorescence detection apparatus of claim 1, wherein the fluorescence detection system comprises a radiation sensitive detector.

9. The fluorescence detection apparatus of claim 8, wherein the radiation sensitive detector includes a detector selected from the group consisting of a photodiode and a photomultiplier.

10. The fluorescence detection apparatus of claim 8, wherein the fluorescence detection system further comprises a peak detector for detecting the formation of fluorescence at visible wavelengths.

11. The fluorescence detection apparatus of claim 10, wherein the peak detector comprises a box-car detector.

12. The fluorescence detection apparatus of claim 1, wherein the fluorescence detection system further comprises a peak detector for detecting the formation of fluorescence at visible wavelengths.

13. The fluorescence detection apparatus of claim 12, wherein the peak detector comprises a box-car detector.

14. The fluorescence detection apparatus of claim 1, wherein the evaluation system comprises a data processing unit.

15. The fluorescence detection apparatus of claim 1, wherein the evaluation system analyzes the detected fluorescence on-line during laser operation.

16. The fluorescence detection apparatus of claim 15, wherein the laser system includes a laser selected from the group of lasers consisting of an ArF, KrF, $F_2$, XeCl and XeF laser.

17. The fluorescence detection apparatus of claim 15, wherein the laser system includes a solid-state laser.

18. The fluorescence detection apparatus of claim 17, wherein the one or more optical components includes a harmonic crystal.

19. A fluorescence detection apparatus for monitoring fluorescence of one or more optical components of a laser system, comprising:

(a) one or more light wave guides for transmitting the fluorescence of the one or more optical components, while the laser system is in operation, wherein the one or more optical components includes at least one selected from the group consisting of one or more laser resonator windows, one or more prisms, one or more etalons, one or more beam splitters, and one or more polarizers;

(b) a fluorescence detection system for detecting the transmitted fluorescence; and (c) an evaluation apparatus for analyzing the detected fluorescence.

20. The fluorescence detection apparatus of claim 19, wherein the one or more light wave guides transmit the fluorescence directly to the fluorescence detection system.

21. The fluorescence detection apparatus of claim 19, wherein the fluorescence detection system comprises an optical filter.

22. The fluorescence detection apparatus of claim 21, wherein the optical filter includes at least one optical filter selected from the group of optical filters consisting of a sharp cut filter and interference filter.

23. The fluorescence detection apparatus of claim 21, wherein the fluorescence detection system further comprises a radiation sensitive detector.

24. The fluorescence detection apparatus of claim 23, wherein the radiation sensitive detector includes a detector selected from the group consisting of a photodiode and a photomultiplier.

25. The fluorescence detection apparatus of claim 19, wherein the fluorescence detection system comprises a radiation sensitive detector.

26. The fluorescence detection apparatus of claim 25, wherein the radiation sensitive detector includes a detector selected from the group consisting of a photodiode and a photomultiplier.

27. The fluorescence detection apparatus of claim 25, wherein the fluorescence detection system further comprises a peak detector for detecting the formation of fluorescence at visible wavelengths.

28. The fluorescence detection apparatus of claim 27, wherein the peak detector comprises a box-car detector.

29. The fluorescence detection apparatus of claim 19, wherein the fluorescence detection system further comprises a peak detector for detecting the formation of fluorescence at visible wavelengths.

30. The fluorescence detection apparatus of claim 29, wherein the peak detector comprises a box-car detector.

31. The fluorescence detection apparatus of claim 19, wherein the evaluation system comprises a data processing unit.

32. The fluorescence detection apparatus of claim 19, wherein the evaluation system analyzes the detected fluorescence on-line during laser operation.

33. The fluorescence detection apparatus of claim 32, wherein the laser system includes a laser selected from the group of lasers consisting of an ArF, KrF, $F_2$, XeCl and XeF laser.

34. The fluorescence detection apparatus of claim 32, wherein the laser system includes a solid-state laser.

35. The fluorescence detection apparatus of claim 32, wherein the one or more optical components includes a harmonic crystal.

36. An excimer or molecular fluorine laser system, comprising:

a laser tube filled with a gas mixture at least including a halogen-containing species and a buffer gas and including therein a heat exchanger for controlling the temperature of the gas mixture and a fan for circulating the gas mixture;

a plurality of electrodes defining a discharge area within the laser tube and connected to a power supply circuit for energizing the gas mixture;

a laser resonator defining a beam path through the discharge area for generating a laser beam; and a fluorescence detection apparatus for monitoring fluorescence of one or more optical components of the laser system, while the laser system is in operation, wherein the one or more optical components includes at least one selected from the group consisting of one or more laser resonator windows, one or more prisms, one or more etalons, one or more beam splitters, and one or more polarizers, the fluorescence detection apparatus comprising:

(a) one or more light wave guides for transmitting the fluorescence of the one or more optical components;

(b) a fluorescence detection system for detecting the transmitted fluorescence; and (c) an evaluation apparatus for analyzing the detected fluorescence.

37. The laser system of claim 36, wherein the one or more light wave glides transmit the fluorescene directly to the fluorescence detection system.

38. The laser system of claim 36, wherein the fluorescence detection system comprises an optical filter.

39. The laser system of claim 38, wherein the optical filter includes at least one optical filter selected from the group of optical filters consisting of a sharp cut filter and interference filter.

40. The laser system of claim 38, wherein the fluorescence detection system further comprises a radiation sensitive detector.

41. The laser system of claim 40, wherein the radiation sensitive detector includes a detector selected from the group consisting of a photodiode and a photomultiplier.

42. The laser system of claim 36, wherein the fluorescence detection system comprises a radiation sensitive detector.

43. The laser system of claim 42, wherein the radiation sensitive detector includes a detector selected from the group consisting of a photodiode and a photomultiplier.

44. The laser system of claim 42, wherein the fluorescence detection system further comprises a peak detector for detecting the formation of fluorescence at visible wavelengths.

45. The laser system of claim 44, wherein the peak detector comprises a box-car detector.

46. The laser system of claim 36, wherein the fluorescence detection system further comprises a peak detector for detecting the formation of fluorescence at visible wavelengths.

47. The laser system of claim 46, wherein the peak detector comprises a boxcar detector.

48. The laser system of claim 36, wherein the evaluation system comprises a data processing unit.

49. The laser system of claim 36, wherein the evaluation system analyzes the detected fluorescence on-line during laser operation.

50. The laser system of claim 49, wherein the laser system includes a laser selected from the group of lasers consisting of an ArF, KrF, $F_2$, XeCl and XeF laser.

51. The laser system of claim 49, wherein the laser system includes a solid-state laser.

52. The laser system of claim 49, wherein the one or more optical components includes a harmonic crystal.

53. The laser system of claim 36, wherein the fluorescence detection apparatus further comprises at least one optical imaging system for collecting fluorescence of at least one of the one or more optical components of the laser system.

54. The fluorescence detection apparatus of claim 53, wherein the at least one optical imaging system comprises one or more plan convex lenses to collect the fluorescence of the at least one optical component.

55. A solid state laser system, comprising:

a solid state laser; and a fluorescence detection apparatus for monitoring fluorescence of one or more optical components of the laser, while the laser system is in operation, the one or more optical components includes at least one selected from the group consisting of one or more laser resonator windows, one or more prisms, one or more etalons, one or more beam splitters, and one or more polarizers, the fluorescence detection apparatus comprising:

(a) one or more light wave guides for transmitting the fluorescence of the one or more optical components;

(b) a fluorescence detection system for detecting the transmitted fluorescence; and (c) an evaluation apparatus for analyzing the detected fluorescence.

56. The laser system of claim 55, wherein the fluorescence detection apparatus further comprises at least one optical imaging system for collecting fluorescence of at least one of the one or more optical components of the laser system.

* * * * *